(12) United States Patent
Bengtson

(10) Patent No.: US 8,171,938 B2
(45) Date of Patent: May 8, 2012

(54) DEVICES, SYSTEMS, AND METHODS FOR LOCATING MAGNETIC INJECTION FILL PORTS

(76) Inventor: Bradley P Bengtson, Grand Rapids, MI (US)

(*) Notice: Subject to any disclaimer, the term of this patent is extended or adjusted under 35 U.S.C. 154(b) by 593 days.

(21) Appl. No.: 12/313,446

(22) Filed: Nov. 20, 2008

(65) Prior Publication Data
US 2009/0137899 A1 May 28, 2009

Related U.S. Application Data

(60) Provisional application No. 61/004,402, filed on Nov. 27, 2007.

(51) Int. Cl.
A61B 19/00 (2006.01)
(52) U.S. Cl. .................. 128/899; 600/424
(58) Field of Classification Search .......... 128/897–899; 600/424; 607/154; 623/66.1; 604/175, 116, 604/117, 288.01–288.04
See application file for complete search history.

(56) References Cited

U.S. PATENT DOCUMENTS

| 4,222,374 | A  | * | 9/1980  | Sampson et al. ............... 128/899 |
| 5,152,757 | A  |   | 10/1992 | Eriksson |
| 5,758,667 | A  |   | 6/1998  | Slettenmark |
| 6,305,381 | B1 | * | 10/2001 | Weijand et al. ............... 128/899 |
| 6,798,193 | B2 | * | 9/2004  | Zimmerman et al. ......... 324/202 |
| 7,255,682 | B1 | * | 8/2007  | Bartol et al. .................. 604/116 |
| 2004/0260147 | A1 |   | 12/2004 | Schulze |
| 2006/0124140 | A1 |   | 6/2006  | Forsell |

OTHER PUBLICATIONS

PCT Notification of Transmittal of International Preliminary Report on Patent Ability, PCT/US08/13053, Jul. 21, 2010.

* cited by examiner

Primary Examiner — John Lacyk
(74) Attorney, Agent, or Firm — Ryan Kromholz & Manion, S.C.

(57) ABSTRACT

Devices, systems, and methods provide accurate and consistent identification of the center of a magnetic infusion port.

21 Claims, 7 Drawing Sheets

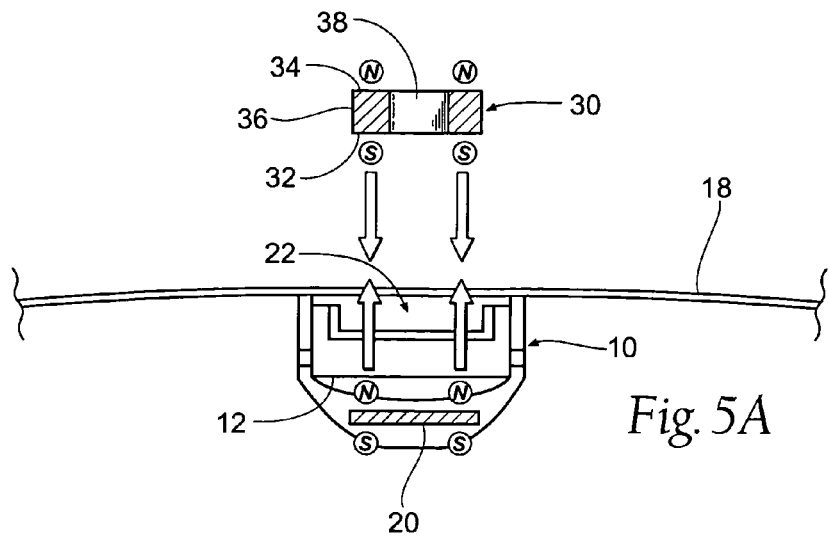
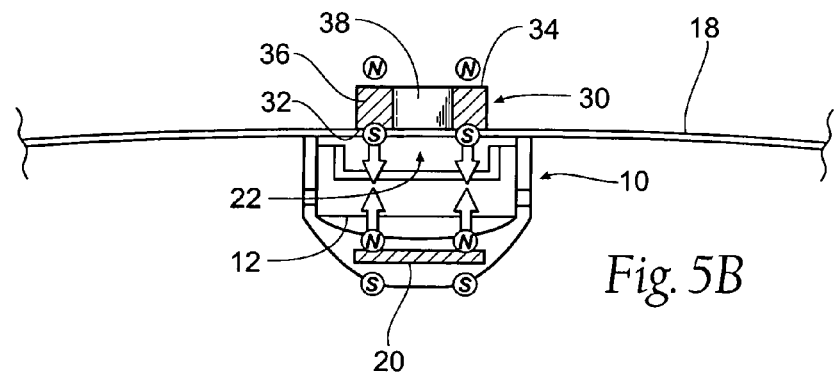
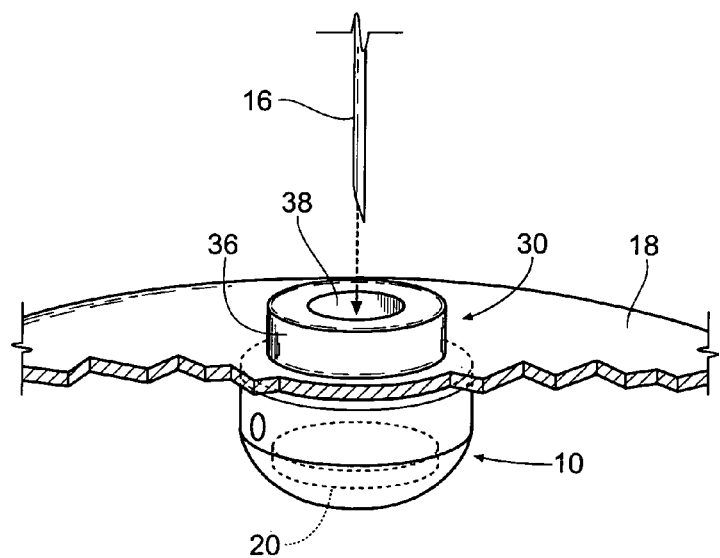

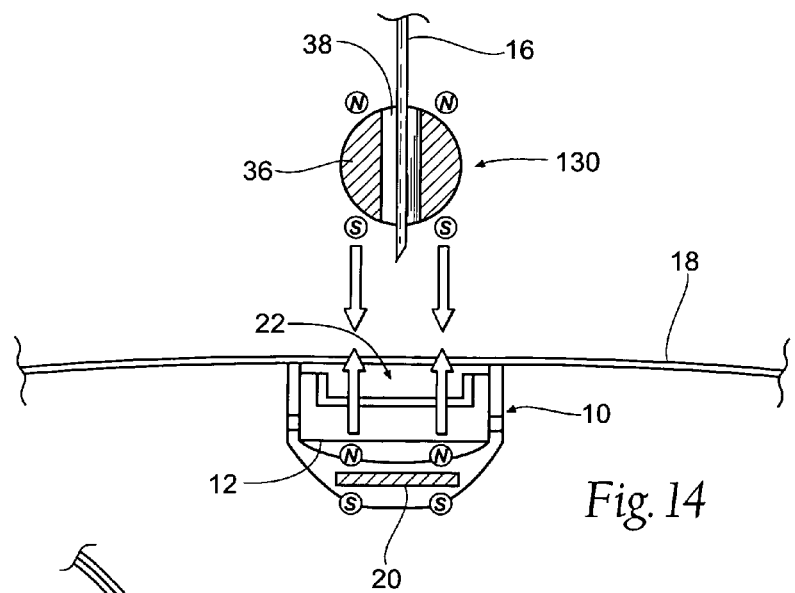
Fig. 14
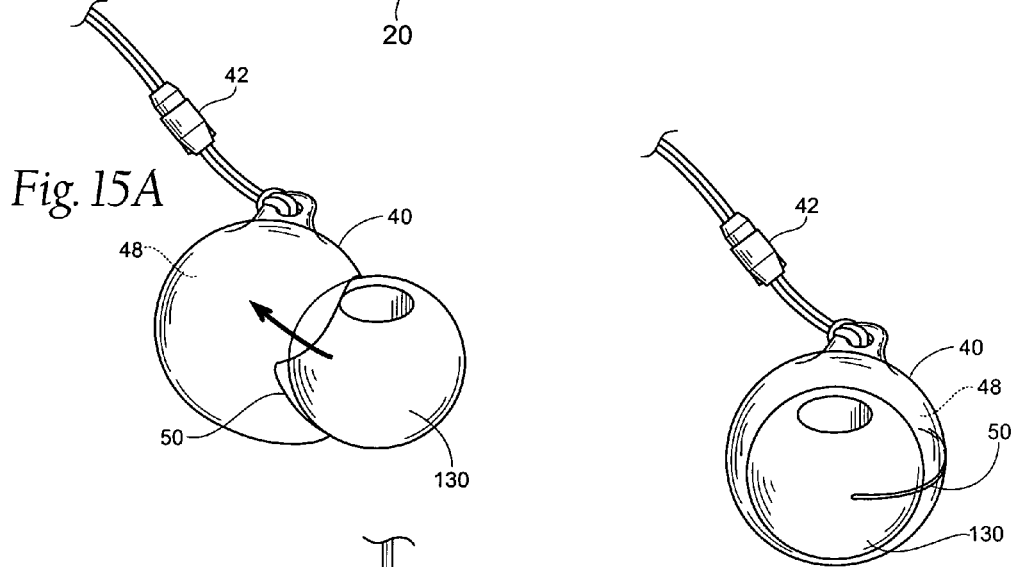
Fig. 15A
Fig. 15B
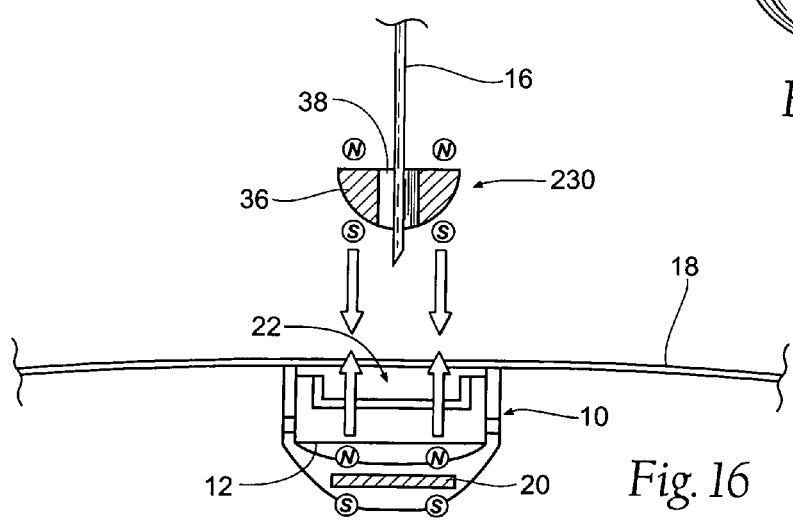
Fig. 16

DEVICES, SYSTEMS, AND METHODS FOR LOCATING MAGNETIC INJECTION FILL PORTS

RELATED APPLICATIONS

This application claims the benefit of co-pending U.S. Provisional Patent Application Ser. No. 61/004,402, filed 27 Nov. 2007.

FIELD OF THE INVENTION

This application relates generally to magnetic injection fill ports used with tissue expanders and like expandable devices.

BACKGROUND OF THE INVENTION

Tissue expanders are commonly used in breast reconstruction and scar revision surgery. Tissue expanders are placed beneath muscle or skin to expand the tissues and allow for the stretching, recruitment and creation of new skin and tissue. The tissue expander is filled with saline solution through a peripheral infusion port.

Conventionally, the infusion port is now integrated on the tissue expander with a magnetic metal backing both to allow for magnetic identification of the expander port and to prevent perforation or rupture of the expander by preventing the needle from puncturing the deep surface. Chemotherapy and other medication infusion devices also have metal backed ports for similar reasons.

A representative magnetic infusion port is disclosed in Rehder et al U.S. Pat. No. 6,588,432, which is incorporated herein by reference. FIGS. 1A and 1B show a magnetic infusion port 10 integrated on a tissue expander 18, as disclosed in the Rehder '432 Patent. As shown in FIGS. 1A and 1B, a needle guard member 12 is positioned spacially from and on the opposite side of the infusion port body 14 from where the needle 16 enters, to prevent the needle from puncturing the infusion port 10 and entering into the tissue expander 18 of the patient. A magnetic material 20 is affixed in the infusion port body outside the infusion port cavity 22 and the needle guard member 12. The magnetic material 20 is positioned outside the infusion port cavity 22 so that its placement does not interfere with the normal and proper insertion of a needle 16 into the infusion port cavity 22. The magnetic material 20 may be any shape or dimension, and made of any magnetically detectable material. For example, the magnetic material 20 may include samarium cobalt or neodymium iron boron, a combination thereof or like material. The outermost perimeter of the magnetic material 20 is spatially aligned with or within the perimeter of the region of the infusion port 10 into which the needle is injected, thus demarcating this region as a target for the needle 16. The magnetic material 20 also has a surface treatment to prevent it from corroding, such as a nickel coating or the like, and is completely enclosed in a polymer, such as a silicone elastomer or the like, to protect it from environmental exposure.

As further described in Rehder '432 Patent (and as shown in FIGS. 2A and 2B), to locate the infusion port 10, a magnetic detection probe 24 is used. The magnetic probe 24 has a polarity opposite to the polarity of the magnetic material 20 of the infusion port that faces the infusion port cavity 22. The magnetic probe 24 is therefore attracted to the magnetic material 20 of the port 10. In use, the probe 24 is scanned across the region of skin containing the port 10. The probe 24 will point to the magnetic material 20 and thereby pivot from a tilted position (when on one side of the magnetic material 20), to an upright position (when over the magnetic material 20, to an opposite tilted position (when on the opposite side of the magnetic material 30). When scanned along an x-axis, and then along a y-axis, the tilt of the probe 24 establishes at least four points of reference A, B, C, D creating a coordinate system. The location for inserting the needle is at the intersection I of two line segments L1 and L2, each defined by a pair of the reference points A and B/C and D established by two passes of the detection probe 24. This intersection I is where the magnetic infusion port 10 is located and where the needle 16 should enter.

FIGS. 3A and 3B show a typical detection probe 24 in use in association with a magnetic infusion port 10 on a tissue expander 18. FIG. 3A shows the probe 24 in a generally vertical position, pointing to the magnetic material 20 of the infusion port 10, indicating that it is magnetically aligned over the magnetic material 20 of the infusion port 10. FIG. 3B shows the probe 24 in tilted position, indicating that it is spaced to a side of the magnetic material 20 of the infusion port 10. The direction of the tilt points to the location of the infusion port 10.

The detection probe 24 used to locate the infusion port 10 adds to the expense of the expansion device 18. Also, in use, the detection probe 24 can be cumbersome to handle. The probe 24 can often stick and lead to inaccurate needle placement. This can, in turn, lead to the accidental perforation of the expander 18 if the needle is not directly introduced into the port 10 or otherwise perforates the silicone shell of the expander 18 at the wrong angle. If the expander 18 is not fully expanded for an adequate time when the expander 18 is prematurely punctured, this may necessitate a less than optimal result or another unnecessary operation to replace the expander 18.

Accurate and precise location of the infusion port 10 as close to its center as possible is critical. Often times the expander 18 is placed very deep to the skin with overlying muscle or fatty tissue. The deeper the expander 18 is in the body, the more difficult it is to identify with the probe 24.

SUMMARY OF THE INVENTION

The invention provides devices, systems, and methods for the identification of the center of a magnetic infusion port.

One aspect of the invention provides a system including an infusion port and a port finder. The infusion may have a magnetic portion, the magnetic portion may have a first surface may have a first magnetic polarity and a second surface may have a second magnetic polarity. The port finder may have a first surface and a second opposite facing surface, the first surface may have a first magnetic polarity and the second surface may have a second opposite magnetic polarity, the port finder may have a center hole extending through the port finder from the first surface to the second surface.

The system may include a sleeve. The sleeve may have an interior cavity sized and configured to receive the port finder. The sleeve may have an opening adjacent the interior cavity, the opening being sized and configured to receive the port finder. The sleeve may have a sticky back side. The back side of the sleeve may have a cover that can be peeled back to expose the sticky material. The back side of the sleeve includes an anesthetic.

The system may include a flexible member coupled to the port finder. The flexible member may be a string.

The port finder center hole may be sized and configured to allow passage of a needle through the center thereof. The port finder center hole may be sized and configured to allow passage of a marking apparatus therethrough.

Another aspect of the invention provides a method including the steps of providing a magnetic infusion port, providing a magnetic port finder, and implanting the magnetic infusion port.

The method may include using the magnetic port finder to locate the magnetic infusion port.

The method may include inserting a needle through the center of the magnetic port finder into the magnetic infusion port.

The method may include marking the location of the magnetic infusion port on the through the center of the magnetic port finder.

The method may include removing the magnetic port finder and inserting a needle into the magnetic infusion port at the marked spot.

The method may include providing a sleeve, inserting the magnet into the sleeve, and using the magnetic port finder to locate the magnetic infusion port.

The method may include providing an adhesive surface on at least one surface of the sleeve.

The method may include inserting a needle through the center of the magnetic port finder into the magnetic infusion port.

The method may include removing the needle from the magnetic infusion port and removing the magnet from the sleeve, the sleeve remaining to serve as a bandage.

The method may include inserting a needle through the center of the magnetic port finder into the magnetic infusion port.

The method may include removing the magnet from the sleeve and inserting a needle through the sleeve into the magnetic infusion port.

The method may include removing the needle from the magnetic infusion port and allowing the sleeve to remain as a bandage.

The method may include placing an anesthetic on the backside of the sleeve.

BRIEF DESCRIPTION OF THE DRAWINGS

FIGS. 5A and 5B are side views, partly in section, showing the magnetic alignment of the port finder shown in FIG. 4 with a conventional magnetic injection port.

FIG. 6 shows the passage of a needle through the center opening of the port finder shown in FIG. 4, when in magnetic alignment with a magnetic injection port as shown in FIG. 5B.

FIG. 14 is a side view, partly in section, showing the magnetic alignment of an alternative embodiment of a port finder with a conventional magnetic injection port.

FIG. 15 shows the port finder of FIG. 14 carried in a sleeve.

FIG. 16 shows an additional alternative embodiment of a port finder.

DESCRIPTION OF REPRESENTATIVE EMBODIMENTS

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figure 1A:
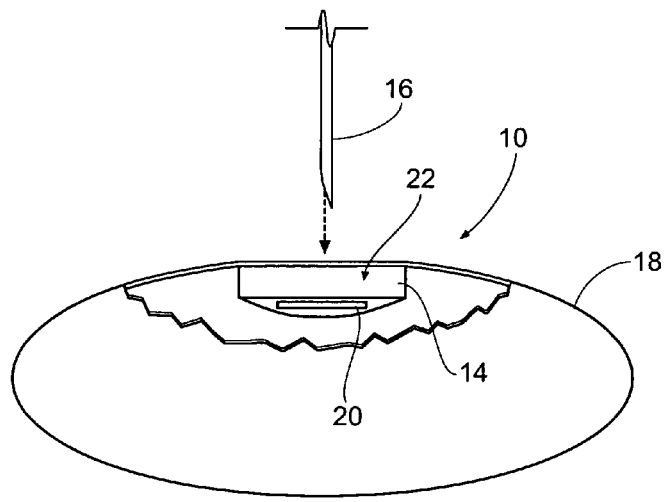
FIGS. 1A and 1B show a prior art magnetic infusion port of the type shown in U.S. Pat. No. 6,588,432.
Figure 1B:
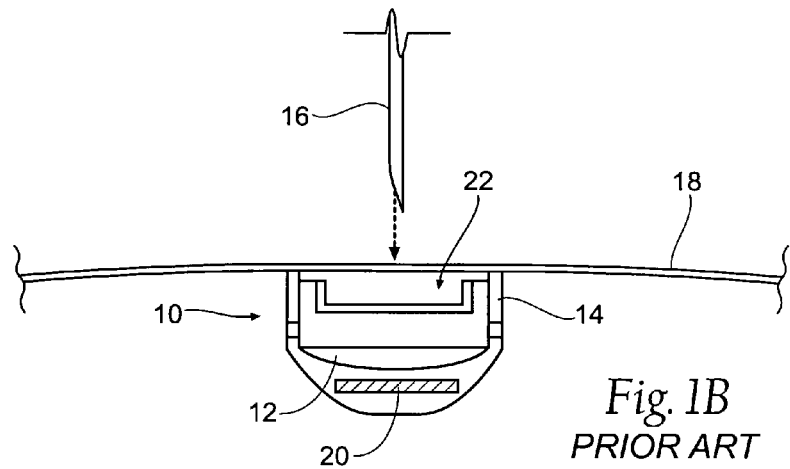
Figure 2A:
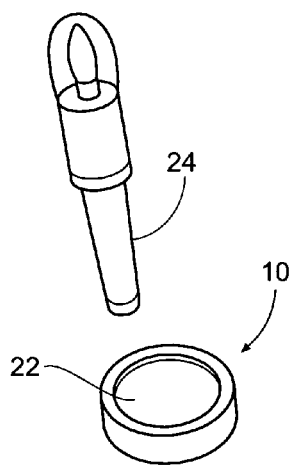
FIGS. 2A and 2B show the use of a prior art magnetic probe in association with the magnetic infusion port shown in FIGS. 1A and 1B.
Figure 2B:
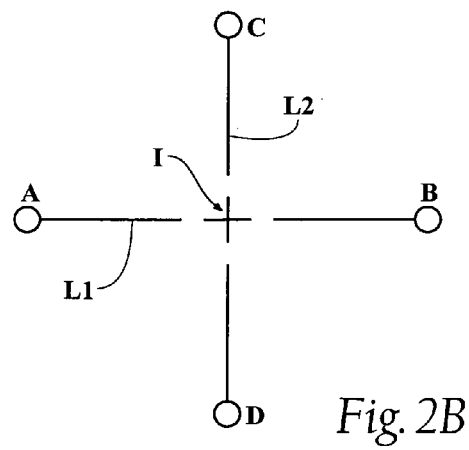
Figure 3A:
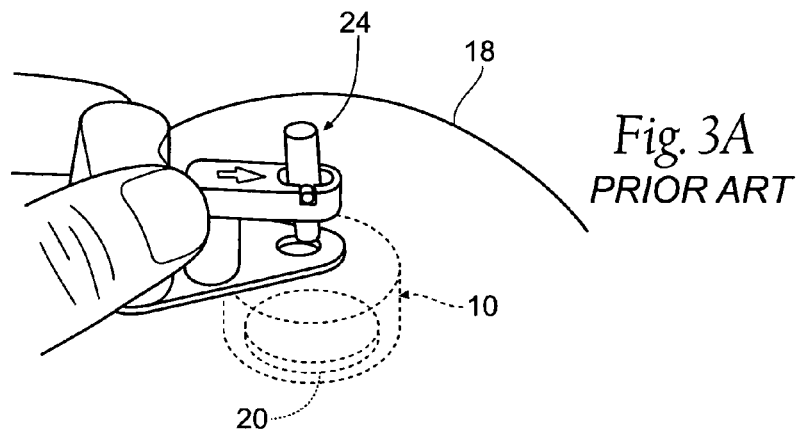
FIGS. 3A and 3B show a conventional magnetic probe in use with a convention magnetic infusion port.
Figure 3B:
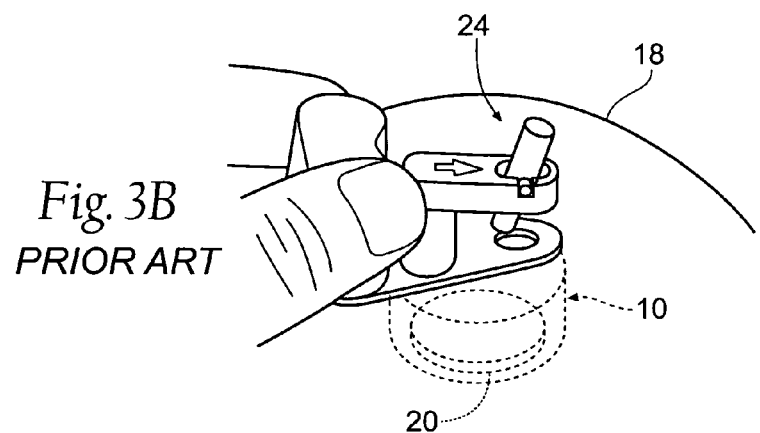
Figure 4:
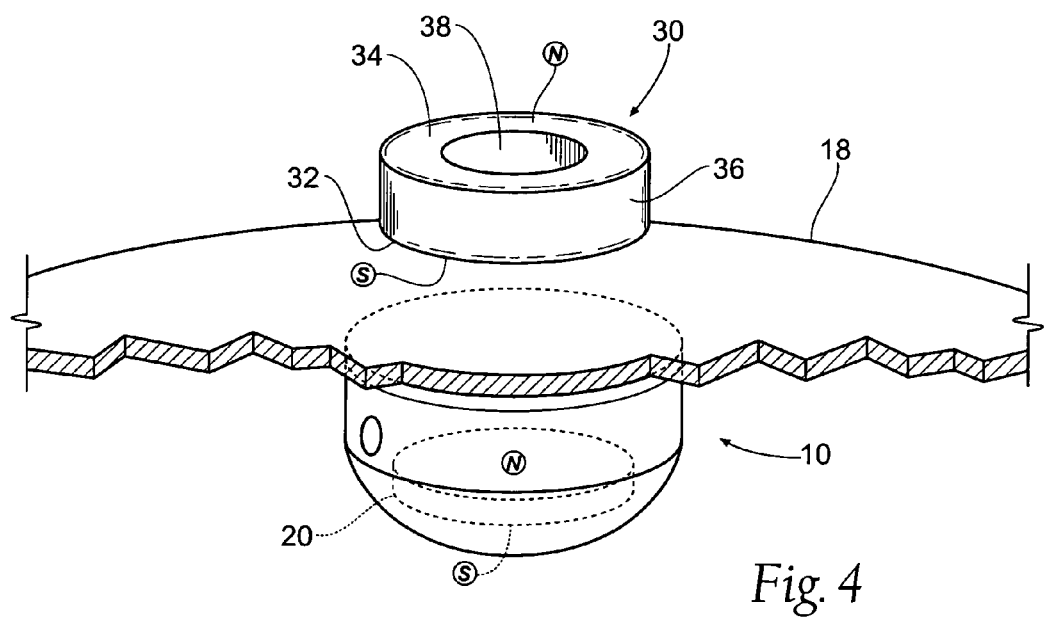
FIG. 4 is a perspective view of a port finder that embodies features of the invention.

FIG. 4 shows a port finder 30 that embodies features of the invention. The port finder 30 comprises a disc having generally flat, opposite facing surfaces 32 and 34. The port finder 30 is made from a magnetic material 36 polarized so that the facing surfaces 32 and 34 present opposite magnetic North and South poles, as indicated in FIG. 4.

As illustrated, the port finder 30 is shaped to generally correspond with the shape of the magnetic material 20 of the infusion port 10, which is typically circular.

Figure 7A:
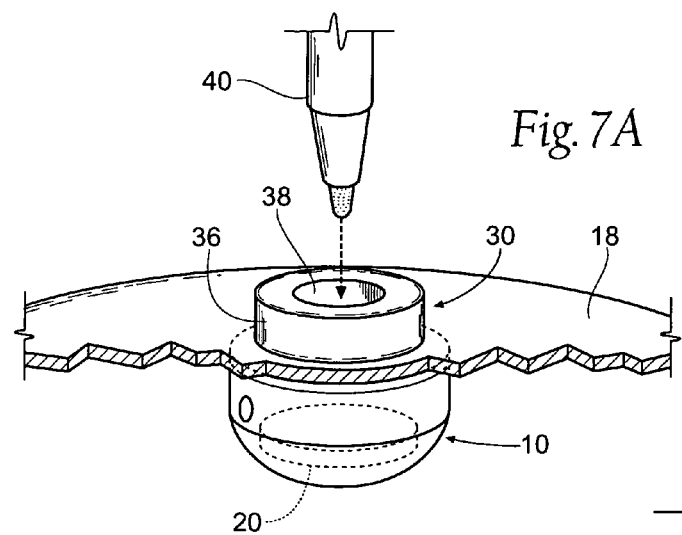
FIGS. 7A and 7B show the use of a marker to mark skin in the center opening of the port finder shown in FIG. 4, when in magnetic alignment with a magnetic injection port as shown in FIG. 5B (FIG. 7A), followed by the removal of the port finder and passage of a needle through the mark (FIG. 7B).

The port finder 30 includes a center hole 38. The hole 38 is sized to at least allow passage of a needle 16 (see FIG. 6). The hole 38 is desirably sized to allow passage of a marker 40, to mark a location on the skin underlying the hole 38 (see FIG. 7A).

As FIGS. 5A and 5B show, and as before described, the magnetic material 20 of the infusion port 10 is polarized to present either a North magnetic-pole or a South magnetic-pole in the direction of the infusion port cavity 22. In the illustrated embodiment, the North magnetic-pole faces the infusion port cavity 22, but the reverse can be true. Magnetic attraction between the North magnetic pole of the material 20 of the infusion port 10 and the opposite South magnetic pole of the magnetic material 36 of the port finder 30, will orient the facing surface of the port finder 30 having the opposite magnetic pole (in FIGS. 5A and 5B, facing surface 32) directly over and in alignment with the magnetic material 20 of the infusion port 10. The center of the hole 38 of the port finder 30 marks the precise location of the exact or near center of the infusion port 10.

Figure 7B:
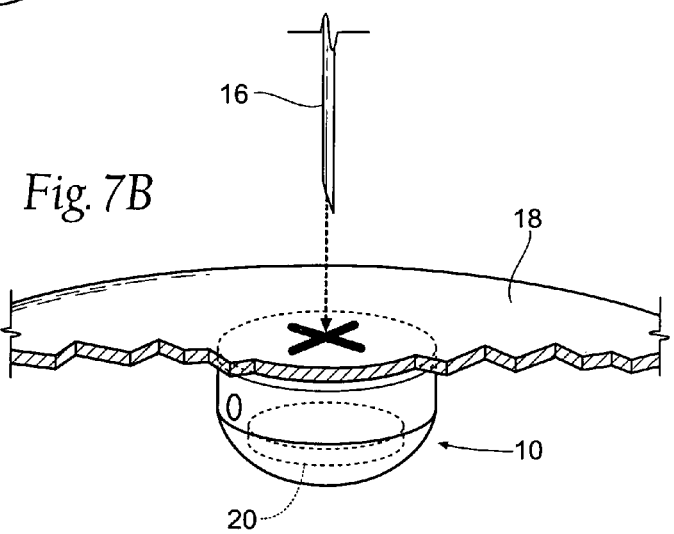

In use (see FIG. 6), the physician can pass the needle 16 through the center of the hole 38 into the infusion port 10. Alternatively (see FIGS. 7A and 7B), the physician can use a marker 40 to first mark the skin in the direct center of the hole 38 (FIG. 7A), then remove the port finder 30, and then pass the needle 16 through the mark to access the port 10 (FIG. 7B).

Figure 8:
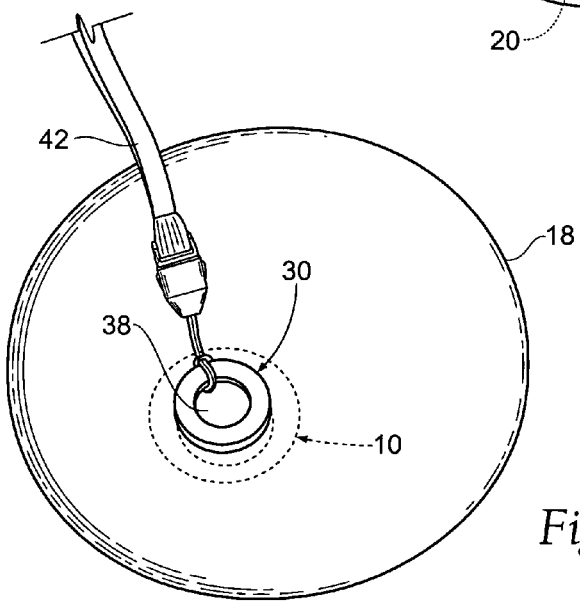
FIG. 8 is a view of the port finder shown in FIG. 4 carried on a lanyard.

In an alternative embodiment (see FIG. 8), the port finder 30 can be attached to a lanyard 42, string or other material and allow for repeated confirmation of the center similar to a pendulum. Left free to swing and pivot on the lanyard 42, the port finder 30 will automatically orient itself with respect to the magnetic material 20 of the infusion port 10, to mark the placement of the needle. The lanyard 42 can also be used for holding or hanging or storing the port finder 30.

Figure 9:
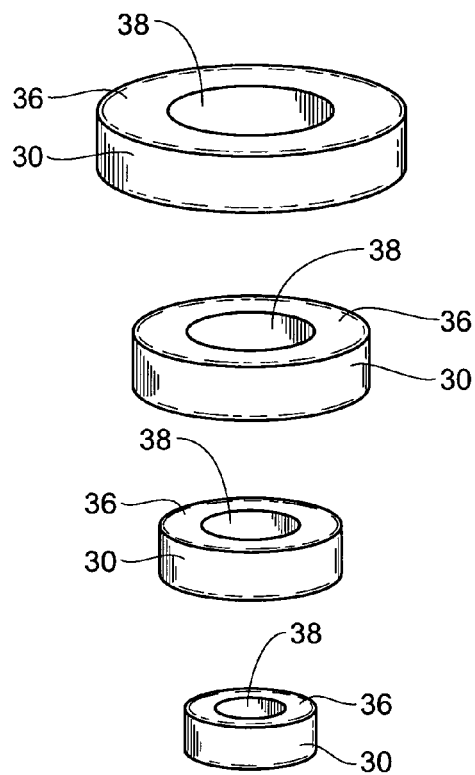
FIG. 9 shows the port finder shown in FIG. 4 in various sizes to accommodate magnetic injection ports of different sizes.

As FIG. 9 shows, the port finder 30 can be variously sized and configured to generally correspond with the size and configuration of typical magnetic field of the port finder 30 should be maximized to the extent possible. Often times, the ports 10 and expanders 18 may be very deep beneath the skin. The deeper they are placed the more difficult to feel and localize the port accurately, and the less the magnetic field of the magnetic material 20 of the port 10 will be at the surface of the skin, so the use of a stronger magnet for the port finder 30 will be of great benefit.

The magnetic fields of the magnetic material 20 of the infusion port 10 and the opposite magnetic field of the port finder 30 accurately and consistently place the center hole 38 of the port finder 30 at the center or near center of the infusion port 10. All surgeons, nurses or patients that surgically place or access tissue expander ports, or chemotherapy or drug infusion ports, will benefit from the use of the port finder 30. The port finder 30 allows for more specific and accurate needle access to the port 10 and decreases the chance of accidental expander or implant puncture and potential unnecessary surgery.

Figure 10A:
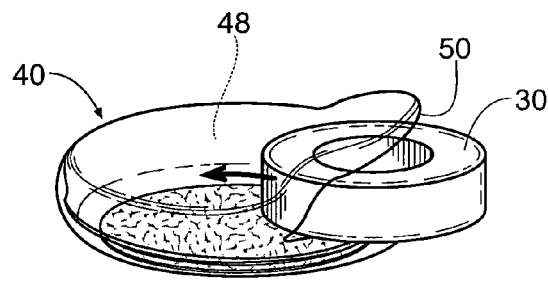
FIG. 10 shows the port finder shown in FIG. 4 carried in a sleeve.
Figure 10B:
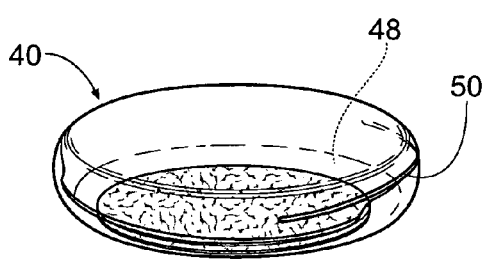
Figure 11:
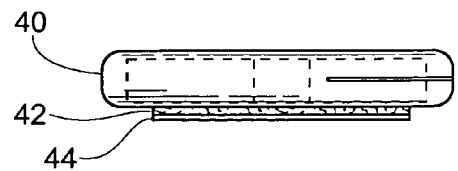
FIG. 11 shows a side view of the sleeve of FIG. 10.

The system may also include a sheath or sleeve 40 as shown in FIGS. 10 and 11. The sleeve 40 is sized and configured to allow the port finder 30 to be placed within the sleeve 40. The sleeve 40 preferably includes a interior cavity 48 sized and configured to receive the port finder 30 and an opening 50 sized and configured to receive the port finder 30. The opening 50 may take any form known in the art, including, but not limited to a slot. Preferably the port finder 30 is inserted in the sleeve by sliding the port finder 30 through the opening 50.

The sleeve 40 is preferably clear and may be made of a plastic or silicon material. The sleeve 40 is preferably disposable. The sleeve 40 may be provided with adhesive 42 on one exterior surface thereof. The adhesive 42 may be of any type known in the art. In this manner, the sleeve 40 may stick to the skin directly and sterilely over the port finder 30 and port 10. The sleeve 40 may further be provided with a removable backing member 44 covering the adhesive 42. The backing member 44 may be of any material known in the art including, but not limited to plastic or paper. It is further contemplated that a topical anesthetic substance 46 may be placed on the side of the sleeve 40 contacting the patient's skin. The anesthetic substance 46 may be applied to the sleeve 40 by the physician, or may be applied to the sleeve 40 during the manufacturing process.

Figure 12A:
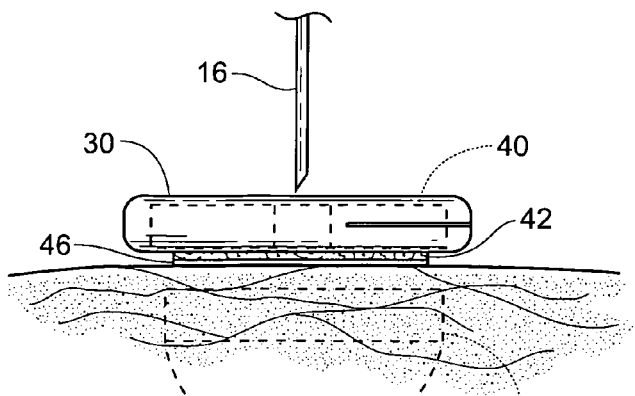
FIGS. 12 and 13 show the passage of a needle through the center opening of the port finder and sleeve shown in FIG. 10, when in magnetic alignment with a magnetic injection port.
Figure 12B:
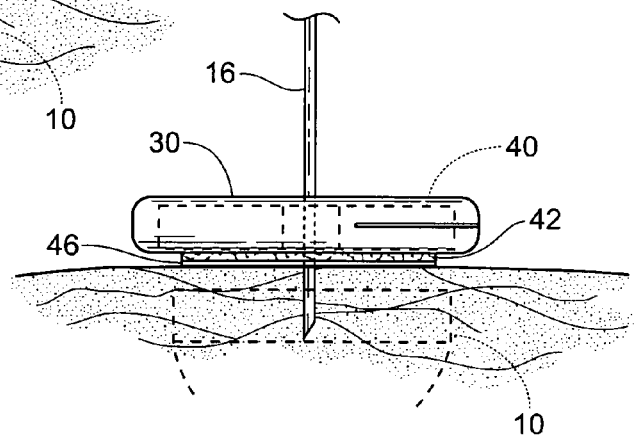
Figure 13A:
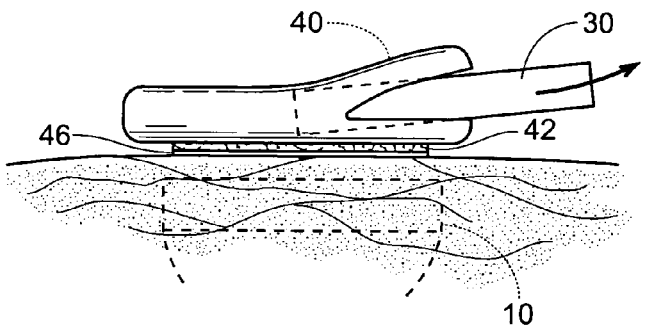
Figure 13B:
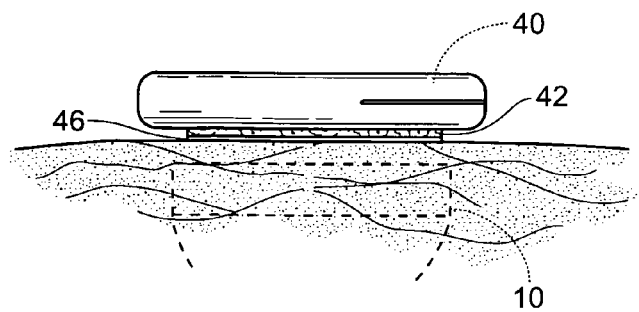

In use, the sleeve 40 may be placed on the port finder 30 as shown in FIG. 10. The backing member 44 may be removed and the port finder 30 may be used to locate the port 10. The physician may then insert a needle 16 through the port 10 as shown in FIG. 12 and 13. The port finder 30 may be removed from the sleeve 40 either before the needle 16 is inserted through the port 10 or after the needle 16 is removed from the port 10. It is contemplated that the sleeve 40 may be left in place to act as a bandage once the needle 16 is removed.

In an alternative embodiment the port finder 130 may have a generally spherical configuration as shown in FIG. 14. The spherical port finder 130 preferably includes a center hole 38 sized and configured for passage of a needle therethrough. The spherical port finder 130 is made from a magnetic material polarized to provide a magnetic North pole and an oppositely disposed magnetic South pole as indicated in FIG. 14. This "Bulls Eye Port Locator" may be well suited for small port locations such as with the LapBand (R) product by Allergan or chemotherapy ports.

It is contemplated that a sleeve 40 made of plastic or silicone as described above may be provided around the spherical port finder 130 and a string or lanyard 42 could be coupled to the sleeve 40 as shown in FIG. 15. The sleeve 40 preferably includes an interior cavity 48 sized and configured to receive the port finder 130 and an opening 50 sized and configured to receive the port finder 130. The opening 50 may take any form known in the art, including, but not limited to a slot. Preferably, the port finder 130 is inserted into the sleeve 40 by sliding the port finder 130 through the opening 50.

As described above the magnetic material 20 of the infusion port 10 is polarized to present either a North magnetic-pole or a South magnetic-pole in the direction of the infusion port cavity 22. In the illustrated embodiment of FIG. 14, the North magnetic-pole faces the infusion port cavity 22, but the reverse can be true. Magnetic attraction between the North magnetic pole of the material 20 of the infusion port 10 and the opposite South magnetic pole of the magnetic material 36 of the spherical port finder 130, will orient the facing surface of the spherical port finder 130 having the opposite magnetic pole (in FIGS. 5A and 5B, facing surface 32) directly over and in alignment with the magnetic material 20 of the infusion port 10. The center of the hole 38 of the spherical port finder 130 marks the precise location of the exact or near center of the infusion port 10.

It is further contemplated that the port finder 230 could have a hemispherical configuration as shown in FIG. 16. The hemispherical port finder preferably includes a center hole 38 sized and configured for passage of a needle therethrough. It is further contemplated that the hemispherical port finder 230 may be used with a sleeve 40 as described above.

The foregoing is considered as illustrative only of the principles and technical features of the invention. Furthermore, since numerous modifications and changes will readily occur to those skilled in the art, it is not desired to limit the invention to the exact construction and operation shown and described. While a representative embodiment has been described, the details may be changed without departing from the principles and technical features of the invention.

I claim:

1. A system for locating an implanted infusion port comprising:
    an infusion port, the infusion port having a magnetic portion, the magnetic portion having a first surface having a first magnetic polarity and a second surface having a second magnetic polarity;
    a port finder, the port finder having a first surface and a second opposite facing surface, the first surface having a first magnetic polarity and the second surface having a second opposite magnetic polarity, the port finder having a center hole extending through the port finder from the first surface to the second surface; and
    a sleeve having an interior cavity sized and configured to receive the port finder.

2. The system of claim 1 wherein the sleeve has an opening adjacent the interior cavity, the opening being sized and configured to receive the port finder.

3. The system of claim 1 wherein the sleeve has a sticky back side.

4. The system of claim 3 wherein the back side has a cover that may be peeled back to expose the sticky material.

5. The system of claim 1 wherein a surface of the sleeve includes an anesthetic.

6. The system of claim 1 further comprising a flexible member coupled to the port finder.

7. The system of claim 6 wherein the flexible member is a string.

8. The system of claim 1 wherein said port finder center hole is sized and configured to allow passage of a needle therethrough.

9. The system of claim 1 wherein said port finder center hole is sized and configured to allow passage of a marking apparatus therethrough.

10. A method comprising:
providing a magnetic infusion port;
providing a magnetic port finder, the magnetic port finder comprising a center aperture extending between a first port finder surface and a second, oppositely disposed port finder surface;
providing a sleeve;
inserting the magnetic port finder into the sleeve;
implanting the magnetic infusion port; and
using the magnetic port finder to locate the magnetic infusion port.

11. The method of 10 further comprising inserting a needle through the center aperture of the magnetic port finder into the magnetic infusion port.

12. The method of claim 10 further comprising marking the location of the magnetic infusion port on the needle through the center aperture of the magnetic port finder.

13. The method of claim 12 further comprising
removing the magnetic port finder; and
inserting a needle into the magnetic infusion port at the marked spot.

14. The method of claim 10 further comprising providing an adhesive substance on at least one surface of the sleeve.

15. The method of claim 14 further comprising inserting a needle through the center aperture of the magnetic port finder into the magnetic infusion port.

16. The method of claim 15 further comprising
removing the needle from the magnetic infusion port; and
removing the magnet from the sleeve, the sleeve remaining to serve as a bandage.

17. The method of claim 14 further comprising
removing the magnet from the sleeve; and
inserting a needle through the sleeve into the magnetic infusion port.

18. The method of claim 17 further comprising
removing the needle from the magnetic infusion port; and
allowing the sleeve to remain to serve as a bandage.

19. The method of claim 10 further comprising placing an anesthetic on at least one surface of the sleeve.

20. A system for locating an implanted infusion port comprising:
an infusion port, the infusion port having a magnetic portion, the magnetic portion having a first surface having a first magnetic polarity and a second surface having a second magnetic polarity; and
a port finder, the port finder having a first pole having a first magnetic polarity and a second pole having a second opposite magnetic polarity, the port finder having a center hole extending through the port finder from the first pole to the second pole; and
a sleeve having an interior cavity sized and configured to receive the port finder.

21. The system of claim 20 wherein the port finder has a generally spherical configuration.

* * * * *